US008082780B2

(12) United States Patent
Vannuffelen et al.

(10) Patent No.: US 8,082,780 B2
(45) Date of Patent: Dec. 27, 2011

(54) METHODS AND APPARATUS FOR DECREASING A DENSITY OF A DOWNHOLE FLUID

(75) Inventors: Stephane Vannuffelen, Southampton (GB); Tsutomu Yamate, Yokohama (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 680 days.

(21) Appl. No.: 12/200,916

(22) Filed: Aug. 28, 2008

(65) Prior Publication Data

US 2010/0050760 A1    Mar. 4, 2010

(51) Int. Cl.
*E21B 49/08* (2006.01)
(52) U.S. Cl. .................................... 73/152.27
(58) Field of Classification Search .............. 73/152.03, 73/152.05, 152.23, 152.27; 166/264
See application file for complete search history.

(56) References Cited

U.S. PATENT DOCUMENTS

| | | | | |
|---|---|---|---|---|
| 3,731,530 | A * | 5/1973 | Tanguy et al. ............. | 73/152.42 |
| 5,329,811 | A * | 7/1994 | Schultz et al. ............. | 73/152.02 |
| 5,587,525 | A * | 12/1996 | Shwe et al. ................ | 73/152.52 |
| 5,635,631 | A * | 6/1997 | Yesudas et al. ............ | 73/61.46 |
| 6,128,949 | A * | 10/2000 | Kleinberg .................. | 73/152.18 |
| 6,939,717 | B2 * | 9/2005 | Jiang et al. ................ | 436/121 |
| 7,196,786 | B2 | 3/2007 | DiFoggio | |
| 7,733,490 | B2 * | 6/2010 | Goodwin et al. ............ | 356/436 |
| 7,913,556 | B2 * | 3/2011 | Hsu et al. .................. | 73/152.28 |
| 2004/0045350 | A1 * | 3/2004 | Jones et al. ................ | 73/152.23 |
| 2004/0231408 | A1 * | 11/2004 | Shammai .................. | 73/152.27 |
| 2006/0243047 | A1 * | 11/2006 | Terabayashi et al. ....... | 73/152.55 |
| 2007/0137293 | A1 * | 6/2007 | Pop et al. .................. | 73/152.23 |

FOREIGN PATENT DOCUMENTS

| | | |
|---|---|---|
| EP | 2028341 A1 | 2/2009 |
| GB | 2359631 A | 8/2001 |
| GB | 2395553 A | 5/2004 |
| WO | 2007/038413 | 4/2007 |
| WO | 2009/064557 A1 | 5/2009 |

* cited by examiner

*Primary Examiner* — John Fitzgerald
(74) *Attorney, Agent, or Firm* — Daryl R. Wright; Jody DeStefanis; Jeff Griffin

(57) ABSTRACT

Methods and apparatus for decreasing a density of a downhole fluid are described. An example apparatus to analyze a downhole fluid includes a chamber to decrease a density of at least a portion of a sample of a downhole fluid. Additionally, the example apparatus includes a sensor to measure a pressure of at least the portion of the sample in the chamber. Further, the example apparatus includes a fluid measurement unit to measure a characteristic of at least the portion of the sample based on a relationship between the pressure of at least the portion of the sample in the chamber and a predetermined pressure. Further yet, the example apparatus includes a control unit to determine a parameter of the downhole fluid based on the characteristic.

27 Claims, 8 Drawing Sheets

METHODS AND APPARATUS FOR DECREASING A DENSITY OF A DOWNHOLE FLUID

FIELD OF THE DISCLOSURE

This patent relates generally downhole fluid analysis and, more particularly, to methods and apparatus for decreasing a density of a downhole fluid.

BACKGROUND

Downhole fluid analysis is often used to provide information in real time about the composition of subterranean formation or reservoir fluids. Such real-time information can be advantageously used to improve or optimize the effectiveness of formation testing tools during sampling processes in a given well (e.g., downhole fluid composition analysis allows for reducing and/or optimizing the number of samples captured and brought back to the surface for further analysis). More generally, collecting accurate data about the characteristics of formation fluid(s) is an important aspect of making reliable predictions about a formation or reservoir and, thus, can have a significant impact on reservoir performance (e.g., production, quality, volume, efficiency, etc.).

Fluid characteristics such as composition, density, viscosity, formation water or formation fluid resistivity, etc. are typically measured using formation fluid testers that are deployed via wireline tools and/or logging-while-drilling (LWD) tools, both types of which are commonly available. Formation fluid testers often use sensors to determine the composition of a sample of formation fluid. Different sensors may be selected to obtain various degrees of specificity in connection with the composition of the formation fluid. However, some of these sensors may be inoperable under certain downhole conditions.

SUMMARY

An example apparatus to analyze a downhole fluid includes a chamber to decrease a density of at least a portion of a sample of a downhole fluid. Additionally, the example apparatus includes a sensor to measure a pressure of at least the portion of the sample in the chamber. Further, the example apparatus includes a fluid measurement unit to measure a characteristic of at least the portion of the sample based on a relationship between the pressure of at least the portion of the sample in the chamber and a predetermined pressure. Further yet, the example apparatus includes a control unit to determine a parameter of the downhole fluid based on the characteristic.

An example method of analyzing a downhole fluid includes obtaining a sample of a downhole fluid and expanding the volume of the sample to decrease a density of at least a portion of the sample. Additionally, the example method includes measuring a pressure of at least the portion of the sample. Further, the example method includes analyzing at least the portion of the sample to determine a parameter of the downhole fluid in response to a relationship between the pressure of at least the portion of the sample and a predetermined pressure.

DETAILED DESCRIPTION

Figure 1:
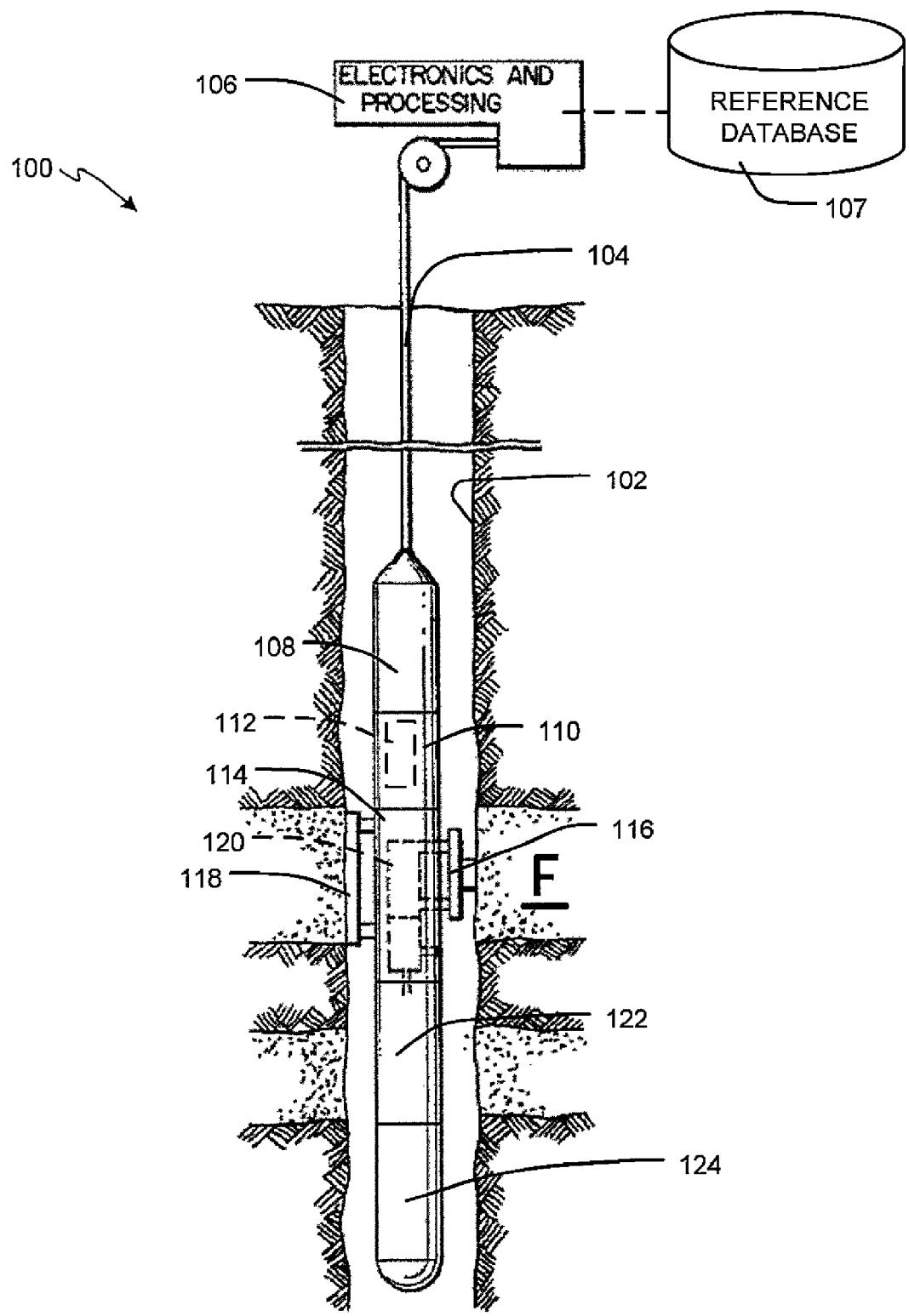
FIG. 1 depicts an example wireline tool that may be used to implement the methods and apparatus described herein.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

The example methods and apparatus described herein can be used to decrease a density of a sample of a downhole fluid within a downhole tool, which may be deployed via a wireline tool, a drillstring, coiled tubing or any other conveyance. In particular, the example methods and apparatus described herein involve obtaining a fluid sample and decreasing the density of the fluid sample prior to analyzing the fluid sample. Additionally, the example methods and apparatus described herein involve measuring the pressure of the sample, moving or changing the pressure of the sample toward a predetermined pressure and analyzing the fluid sample.

Alternatively, example methods and apparatus described herein involve decreasing the pressure of the sample to within an acceptable deviation from the predetermined pressure without automatically controlling or changing the pressure of the sample after the sample is within the chamber and analyzing the sample. In these examples, a chamber may be sized to allow an injected fluid sample to expand such that the pressure and/or density of the injected fluid sample decreases to within the acceptable deviation from the predetermined pressure. In particular, in the illustrated examples described herein, the density of the fluid sample can be decreased by actuating a valve to an open position to enable a fluid to flow into a chamber. The volume of the chamber enables the volume of the sample that enters the chamber to increase and decreases the density and the pressure of the sample. In some examples, enabling the fluid to enter the chamber initiates a phase separation of a portion of the sample from a liquid phase to a gaseous phase.

Decreasing the density of the sample enables the example methods and apparatus described herein to utilize sensors and/or fluid measurement units that may only be operable, effective, or accurate below certain pressures and which may only be able to obtain measurements from portions of fluid samples in a gaseous phase. Additionally, some elements or components of formation fluids (e.g., hydrogen sulfide) are relatively difficult to measure when the fluid sample is at a relatively high pressure and/or in a liquid phase. Utilizing the methods and apparatus described herein enables these previously difficult to measure elements and/or components of formation fluids to be more accurately measured in a downhole environment.

In one described example, a predetermined amount of fluid enters a sample chamber and the pressure and density of the fluid in the chamber decrease. In a case where the fluid entering the chamber is a liquid, the decreasing pressure may induce a phase separation so that some of the fluid in the chamber is in a gaseous phase while some of the fluid remains in a liquid phase. In other cases where the fluid entering the chamber is a gas, the decrease in pressure may result in a less dense gas. In any case, after the fluid has entered the chamber, a valve is actuated to a closed position and a sensor measures the pressure of the sample within the chamber. The measured pressure is then compared to a predetermined pressure to determine if the pressure within the chamber should be changed toward the predetermined pressure. Once the pressure of the sample within the chamber is the same as or within an acceptable deviation from the predetermined pressure, a fluid measurement unit measures characteristics and/or parameters of a gaseous portion of the sample within the chamber. These measured values are compared to known values stored within a reference database to determine the composition of the fluid sample. Once a requisite number of measurements have been obtained from the fluid sample within the chamber, the valve is actuated to the open position and the pressure is increased within the chamber to encourage the sample to flow from the chamber back into a flowline of the downhole tool.

FIG. 1 depicts an example wireline tool 100 that may be used to extract and analyze formation fluid samples and which may be used to decrease a density of a fluid sample using the example methods and apparatus described herein. As shown in FIG. 1, the example wireline tool 100 is suspended in a borehole or wellbore 102 from the lower end of a multiconductor cable 104 that is spooled on a winch (not shown) at the surface. At the surface, the cable 104 is communicatively coupled to an electronics and processing system 106. The electronics and processing system 106 may include or may be communicatively coupled to a reference database 107 that may be used to store reference measurement values of reference formation fluids known to have particular fluid compositions, parameters or characteristics. The wireline tool 100 includes an elongated body 108 that includes a collar 110 having a downhole control system 112 configured to control extraction of formation fluid from the formation F, measurements performed on the extracted fluid as well as to control the example apparatus described herein.

The example wireline tool 100 also includes a formation tester 114 having a selectively extendable fluid admitting assembly 116 and a selectively extendable tool anchoring member 118 that are respectively arranged on opposite sides of the body 108. The fluid admitting assembly 116 is configured to selectively seal off or isolate selected portions of the wall of the wellbore 102 to fluidly couple the adjacent formation F and draw fluid samples from the formation F. The formation tester 114 also includes a fluid analysis module 120 through which the obtained fluid samples flow. The fluid may thereafter be expelled through a port (not shown) or it may be sent to one or more fluid collecting chambers 122 and 124, which may receive and retain the formation fluid for subsequent testing at the surface or a testing facility.

In the illustrated example, the electronics and processing system 106 and/or the downhole control system 112 are configured to control the fluid admitting assembly 116 to draw fluid samples from the formation F and to control the fluid analysis module 120 to measure the fluid samples. In some example implementations, the fluid analysis module 120 may be configured to analyze the measurement data of the fluid samples as described herein. In other example implementations, the fluid analysis module 120 may be configured to generate and store the measurement data and subsequently communicate the measurement data to the surface for analysis at the surface. Although the downhole control system 112 is shown as being implemented separate from the formation tester 114, in some example implementations, the downhole control system 112 may be implemented in the formation tester 114.

As described in greater detail below, the example wireline tool 100 may be used in conjunction with the example methods and apparatus to measure characteristics of a fluid sample to determine a parameter(s) of the fluid. For example, the formation tester 114 may include one or more fluid analyzers or fluid measurement units disposed adjacent a chamber or a flowline that may be controlled by one or both of the downhole control system 112 and the electronics and processing system 106 to determine the composition of or a characteristic of fluid samples extracted from, for example, the formation F. In addition, in accordance with the example methods and apparatus described herein, the formation tester 114 is provided with various means to decrease the density of a fluid sample and to obtain measurements of that fluid sample.

While the example methods and apparatus to decrease the density of a sample of a downhole fluid are described in connection with a wireline tool such as that shown in FIG. 1, the example methods and apparatus can be implemented with any other type of wellbore conveyance. For example, the example methods and apparatus can be implemented with a drill string including LWD and/or measurement-while-drilling (MWD) modules, coiled tubing, etc.

Figure 2:
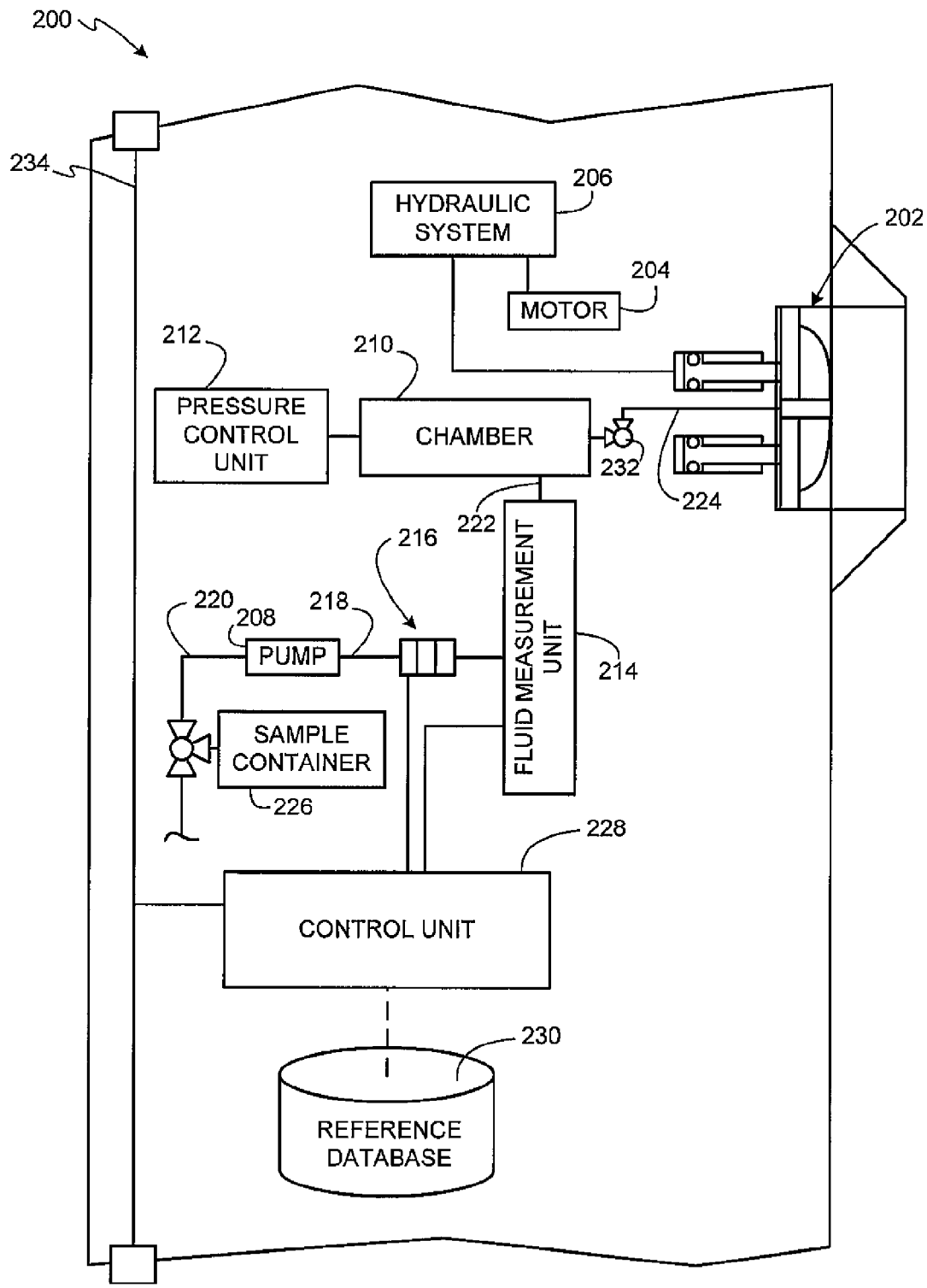
FIG. 2 is a simplified schematic illustration of an example manner in which the formation tester of FIG. 1 may be implemented.

FIG. 2 is a simplified schematic illustration of an example formation sampling tool 200 that may be used to implement the formation tester 114 of FIG. 1. The example formation sampling tool 200 includes a probe assembly 202 that can be selectively engaged to a surface of a wellbore via a motor 204 and a hydraulic system 206 to draw fluids from a formation. In other example implementations, straddle packers (not shown) can additionally or alternatively be used to engage and isolate a portion of the surface of the wellbore to draw fluids from a formation. The formation sampling tool 200 is also provided with a pump 208 that may be used to draw fluids from a formation into the formation sampling tool 200.

The formation sampling tool 200 includes a chamber 210 to decrease the density and/or the pressure of a fluid sample extracted from, for example, the formation F. The chamber 210 is coupled to a pressure control unit 212 that changes the pressure of the fluid sample within the chamber 210 toward a predetermined pressure. However, as described below, in other example implementations, the formation sampling tool 200 may not be provided with the pressure control unit 212. The formation sampling tool 200 also includes one or more fluid sensors to measure characteristics of the fluids drawn into the formation sampling tool 200. More specifically, in the illustrated example, the formation sampling tool 200 is provided with a fluid measurement unit 214 to measure one or more characteristics of formation fluids. The formation fluids may comprise at least one of a heavy oil, a bitumen, a gas condensate, a drilling fluid, a wellbore fluid or a fluid extracted from a subsurface formation. The fluid measurement unit 214 may be implemented using, for example, a light absorption spectrometer having a plurality of channels, each of which may correspond to a different wavelength. In other example implementations, the fluid measurement unit 214 may be implemented using an infrared spectrometer, a tunable laser spectrometer, an acusto-optical tunable filter spectrometer, an optical absorption spectrometer, an LED spectrometer (e.g., a temperature controlled LED and optical filter spectrometer), a LED array spectrometer, a wavelength modulation spectrometer, a cavity ring-down spectrometer, an ultraviolet spectrometer, an ultraviolet-visible spectrometer, a near infrared spectrometer, a mid-infrared spectrometer, a UV/VIS/NIR spectrometer, or a plasma spectrometer. In some examples, a plasma spectrometer refers to an Inductive Coupled Plasma (ICP) chemical analysis device. In practice, if a plasma spectrometer is used to implement the formation sampling tool 200, the sample is initially vaporized, the vaporized sample is at least partially turned into a plasma, and light emitted from the plasma may then be analyzed to determine the composition of the sample. Alternatively or additionally, the fluid measurement unit 214 may be implemented using a metal corrosion measurement unit, an optical reflection measurement unit, or a solid state gas sensor. Each of the above described implementations of the fluid measurement unit 214 may be used to measure spectral information for fluids drawn from a formation and/or to measure any other characteristic(s) of the fluids. Such spectral information may include characteristic values such as optical density values associated with each of the channels and may be used, for example, to determine the composition of the fluid(s).

The formation sampling tool 200 is also provided with one or more sensors 216 to measure pressure, temperature, density, fluid resistivity, viscosity, and/or any other fluid properties or characteristics. While the sensors 216 are depicted as being in-line with a flowline 218, one or more of the sensors 216 may be used in other flowlines 220, 222 or 224 or adjacent the chamber 210 within the example formation sampling tool 200. To measure fluid characteristics, the one or more sensors 216 and/or the fluid measurement unit 214 are in contact with or exposed to the fluid(s) in the chamber 210 and/or the flowlines 218, 220, 222, or 224. The formation sampling tool 200 may also include a fluid sample container or store 226 including one or more fluid sample chambers in which formation fluid(s) recovered during sampling operations can be stored and brought to the surface for further analysis and/or confirmation of downhole analyses. In other example implementations, the fluid measurement unit 214 and/or the sensors 216 may be positioned in any other suitable position such as, for example, between the pump 208 and the fluid sample container or store 226.

Figure 8:
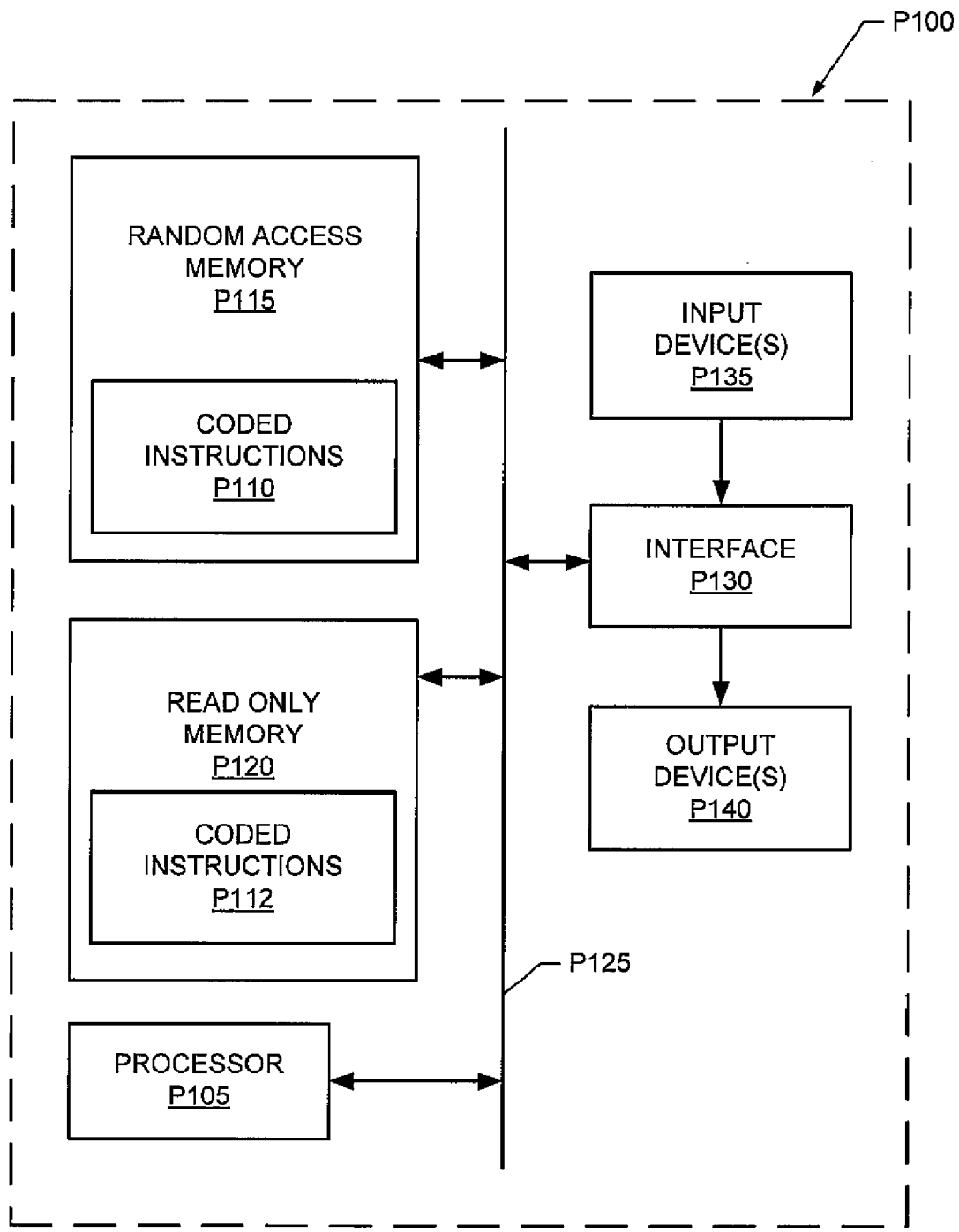
FIG. 8 is a schematic illustration of an example processor platform that may be used and/or programmed to implement any or all of the example methods and apparatus described herein.

To store, analyze and/or process test and measurement data (or any other data acquired by the formation sampling tool 200), the formation sampling tool 200 is provided with a control unit 228 that may be communicatively coupled to a reference database 230 that may be used to store measurement values obtained from the fluid sample and/or reference measurement values of reference formation fluids known to have particular fluid compositions. The control unit 228 may be generally implemented as shown in FIG. 8. In the illustrated example, the control unit 228 may include a processor (e.g., a CPU and random access memory such as shown in FIG. 8) to control operations of the formation sampling tool 200 and implement measurement routines. For example, the control unit 228 may be used to control the fluid measurement unit 214 to perform spectral measurements of fluid characteristics of formation fluid and to actuate a valve 232 to enable a fluid sample to flow from the flowline 224 into the chamber 210 to reduce the density and/or the pressure of the fluid sample within the chamber 210. The control unit 228 may further include any combination of digital and/or analog circuitry needed to interface with the sensors 216 and/or the fluid measurement unit 214.

To store machine readable instructions (e.g., code, software, etc.) that, when executed by the control unit 228, cause the control unit 228 to implement measurement processes or any other processes described herein, the control unit 228 may be provided with an electronic programmable read only memory (EPROM) or any other type of memory (not shown). To communicate information when the formation sampling tool 200 is downhole, the control unit 228 is communicatively coupled to a tool bus 234, which may be communicatively coupled to a surface system (e.g., the electronics and processing system 106).

Although the components of FIG. 2 are shown and described above as being communicatively coupled and arranged in a particular configuration, the components of the formation sampling tool 200 can be communicatively coupled and/or arranged differently than depicted in FIG. 2 without departing from the scope of the present disclosure. In addition, the example methods and apparatus described herein are not limited to a particular conveyance type but, instead, may be implemented in connection with different conveyance types including, for example, coiled tubing, wireline, wired-drillpipe, and/or other conveyance means known in the industry.

Figure 3:
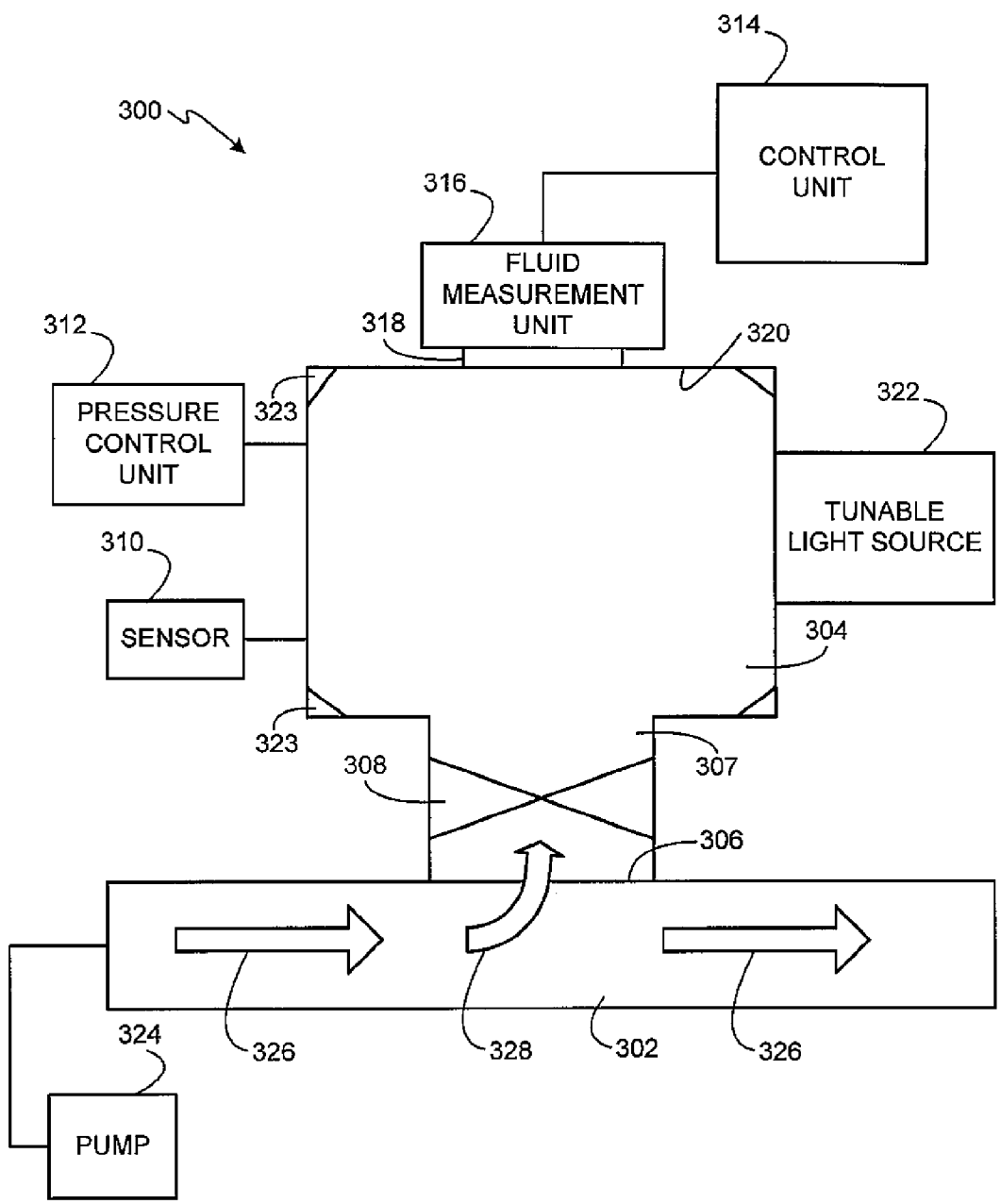
FIG. 3 is a schematic illustration of an example apparatus that may be used to implement or in conjunction with the fluid measurement unit of FIG. 2.

FIG. 3 illustrates an example apparatus 300 that may be used to implement a portion of the formation sampling tool 200 associated with the chamber 210, the pressure control unit 212, the fluid measurement unit 214, the sensors 216 and/or the valve 232 of FIG. 2. The example apparatus 300 includes a flowline 302 that is fluidly coupled to a chamber 304 at an opening 306 via a flowline section 307. A valve 308 is positioned adjacent the opening 306 within the flowline section 307 to control fluid flow between the flowline 302 and the chamber 304. The valve 308 may open to enable fluid to flow into or out of the chamber 304 or the valve 308 may close to retain at least a portion of the sample within the chamber 304. The valve 308 may be any suitable valve that may be operable within subterranean formation conditions such as, for example, an injection valve that may be a micro-injection valve, a rotary micro-injection valve, a rotary injection valve, or a sliding micro-injection valve, etc.

The chamber 304 and the valve 308 may be used to implement the chamber 210 and the valve 232 of FIG. 2, respectively. In the illustrated example, the chamber 304 and the valve 308 may be advantageously used to decrease the density and/or the pressure of at least a portion of the sample by enabling a volume of the sample to increase. Specifically, the chamber 304 may enable a phase of the portion of the sample to change from a liquid phase to a gaseous phase once the sample enters the chamber 304. If the sample is in a gaseous phase once it enters the chamber 304, the spectrum line width of the sample may be relatively narrow and, thus, a wavelength modulation spectrometer may be operable. In some examples, the chamber 304 may enable the pressure of the sample to decrease below a bubble point pressure. Alternatively, the chamber 304 may enable the portion of the sample to change from a relatively dense gas to a relatively less dense gas once the sample enters the chamber 304.

Typically, fluids drawn from subsurface formations are under considerable amounts of pressure and, thus, these fluids may have relatively high densities. This high pressure contributes to certain fluids being in a liquid phase at a formation pressure, while these same fluids would be in a gaseous phase at an atmospheric pressure. Unfortunately, some sensors and/or fluid measurement units may only be operable below a pressure threshold such as, 1.5 bar, and/or these devices may only be able to obtain fluid measurements from samples in a gaseous phase. Sensors and/or fluid measurement units that may only be operable under certain downhole conditions include cavity ring-down spectrometers, wavelength modulation spectrometers or spectrometers that are used in conjunction with a tunable light source (e.g., a temperature controlled tunable diode laser, a temperature controlled broadband fiber light source, an amplified spontaneous emission source, a temperature controlled microelectromechanical system (MEMS) tunable filter, or a temperature controlled tunable fiber laser). These fluid measurement units and sensors are often able to measure significantly more detailed characteristics of the fluid sample, which results in a more accurate representation of the composition of the sample as compared to other fluid measurement units or sensors operable at relatively high pressures or that obtain measurements from samples in a liquid phase. Additionally, fluids at relatively low pressures have more absorption peaks as compared to fluids at relatively high pressures. These absorption peaks are associated with one or more measurable characteristics of the fluid and, thus, the more absorption peaks that the fluid has, the more accurate the characterization of the fluid composition may be. In the example apparatus 300, the volume of the chamber 304 enables a pressure of the fluid within the chamber 304 to be significantly reduced and, thus, the above-referenced fluid measurement units and/or sensors, which were previously unable to be used to measure formation fluids downhole under certain subsurface formation conditions, may now be implemented using the example methods and apparatus described herein.

Generally, fluids extracted from subsurface formations at different depths are under different amounts of pressure and, therefore, to measure a pressure of the sample within the chamber 304 and to compensate for these pressure differences, the example apparatus 300 is provided with a sensor 310 and a pressure control unit 312 that may be used to implement the sensors 216 and the pressure control unit 212 of FIG. 2. Specifically, the sensor 310 may measure the pressure of the fluid within the chamber 304 and a control unit 314 may compare the measured pressure to a predetermined pressure. If there is a difference between the measured pressure and the predetermined pressure, the pressure control unit 312 may change the pressure of the sample within the chamber 304 toward the predetermined pressure. For example, if the pressure measured by the sensor 310 is 1.1 bar and the predetermined pressure is 1.5 bar, the pressure control unit 312 may increase the pressure of the sample within the chamber 304 toward the predetermined pressure (i.e., 1.5 bar in this example). Additionally, changing the pressure of the sample within the chamber 304 enables the spectrum line width of the sample to be controlled and, thus, for example, a wavelength modulation spectrometer may be operable. Further, changing the pressure of the sample within the chamber 304 may advantageously control the temperature of the sample within the chamber 304. After the pressure control unit 312 changes the pressure of the sample within the chamber 304, the sensor 310 again measures the pressure and the measured pressure is compared to the predetermined pressure by the control unit 314.

However, in other example implementations, the example apparatus 300 may not be provided with the pressure control unit 312. In this example the size and/or volume of the chamber 304 may be associated with decreasing the pressure of the sample toward the predetermined pressure. In particular, if the approximate pressure of the formation is known (e.g., 400 bar), the size of the chamber 304 may be such that once the sample enters the chamber 304 the pressure of the sample reduces to within an acceptable deviation from the predetermined pressure (e.g., 1.5 bar). However, in other examples, the chamber 304 may be sized according to the pressure of the formation to change the pressure of the sample to any other predetermined pressure (e.g., 1.0 bar, 1.5 bar, 2.0 bar, etc.).

To measure a characteristic of a portion of the sample once the measured pressure is the same as or within an acceptable deviation from the predetermined pressure, the example apparatus 300 is provided with a fluid measurement unit 316. The fluid measurement unit 316 is provided with a window 318 (e.g., an optical window) that is substantially adjacent a surface 320 of the chamber 304. The window 318 may be implemented using any suitable material such as a scratch resistant material (e.g., a sapphire material). The window 318 may be substantially flush with the surface 320 or the window 318 may be partially positioned within the chamber 304.

In other example implementations, the fluid measurement unit 316 may be a metal corrosion measurement unit. The metal corrosion measurement unit may be provided with a single electrode (not shown) that is at least partially positioned within the chamber 304. The electrode is electrically coupled to a plate or a metallic plate that is exposed to the fluid within the chamber 304. The metal corrosion measurement unit measures the resistivity of the plate while the plate is exposed to the fluid. As the fluid or a component within the fluid (e.g., hydrogen sulfide or carbon dioxide) corrodes the plate, the measured resistivity increases. The rate at which the fluid corrodes the plate and, thus, the rate at which the resistivity increases is associated with the species and/or analyte(s) present within the fluid. In other examples, the fluid measurement unit 316 may be a corrosion monitoring unit that can detect changes in a surface as the surface is exposed to the fluid. For example, as the fluid corrodes the plate the intensity and/or the amount of reflected light from the surface may decrease. Specifically, a color of the surface may change, which may indicate the presence of a particular component within the fluid.

In other example implementations, the fluid measurement unit 316 may be an optical reflection measurement unit or an optical absorption spectrometer using, for example, the technique of attenuated total reflectance (ATR). The optical reflection measurement unit may be advantageously used to measure both the hydrogen sulfide and the carbon dioxide in the portion of the sample within the chamber 304. Generally, the absorption rate of hydrogen sulfide is relatively low and the absorption rate of carbon dioxide is relatively high. Therefore, to determine the absorption rate of the sample within the chamber 304 and to accurately detect the presence and/or concentration of hydrogen sulfide and carbon dioxide in the sample, the optical measurement unit may measure light reflected off of the window 318 to determine the absorption of the sample within the chamber 304. The measured absorption is associated with the species and/or analyte(s) present within the fluid.

Generally, the fluid measurement unit 316 may be configured to measure at least the spectral characteristics of a gaseous portion of the sample within the chamber 304. In some examples, the fluid measurement unit 316 may be configured to measure a single wavelength (e.g., a wavelength parameter) or a plurality of wavelengths (e.g., a plurality of wavelength parameters). The parameter measurement values obtained using the fluid measurement unit 316 may be used to identify particular species and/or analyte(s) present in the fluid sample based on a comparison of the parameter measurement values with known parameter values stored in, for example the reference database 107 (FIG. 1) or 230 (FIG. 2). The known parameter values may be reference values that were obtained from similar subterranean formations. Alternatively, the known parameter values may have been generated from laboratory experiments under controlled conditions.

To transmit a light wavelength or a range of light wavelengths through a portion of the sample within the chamber 304, the example apparatus 300 is provided with a tunable light source 322. Generally, the tunable light source 322 transmits one or more light wavelengths) through the sample and an intensity and/or a parameter of the light wavelength(s) is measured by the fluid measurement unit 316 once the light has passed through the sample. The intensity and/or the parameter of the light wavelength(s) corresponds to absorption characteristics of the sample, which are associated with the analyte(s) or chemical species present in fluid sample. Typically, the light is transmitted through a portion of sample in a gaseous phase.

The tunable light source 322 may be any suitable tunable light source such as, for example, a temperature controlled tunable diode laser, a temperature controlled broadband fiber light source, an amplified spontaneous emission source, a temperature controlled microelectromechanical system (MEMS) tunable filter or a temperature controlled tunable fiber laser. In some example implementations, the example apparatus 300 may be provided with a multipath optical cell 323 that may reflect the light wavelength(s) emitted by the tunable light source 322 to increase the amount of exposure that the fluid within the chamber 304 has to the light wavelength(s). Generally, the more exposure the sample has to the light wavelength(s), the higher the absorption levels within the sample. For example, hydrogen sulfide has a relatively low absorption level, but increasing the amount of exposure that the hydrogen sulfide has to the light wavelength(s), increases the total absorption by the hydrogen sulfide.

In operation, a pump 324, which may be used to implement the pump 208 of FIG. 2, pumps fluid (e.g., formation fluid) through the flowline 302 in a direction generally indicated by arrows 326. As the fluid moves through the flowline 302, the valve 308 may actuate to an open position to enable a sample of the fluid to flow through the opening 306, the flowline section 307 and the valve 308 into the chamber 304 in a direction generally indicated by arrow 328. As the sample enters the chamber 304, the density and pressure of the sample is reduced which, in turn, may induce a phase separation of a portion of the sample within the chamber 304. Specifically, as the sample enters the chamber 304, a portion of the sample is vaporized. Once a predetermined amount of fluid has entered the chamber 304 or a predetermined amount of time has expired, the valve 308 is actuated to a closed position to capture the sample within the chamber 304.

The sensor 310 then measures the pressure of the sample within the chamber 304 and the measured pressure is compared to a predetermined pressure by the control unit 314. In some examples, the predetermined pressure is a pressure that was used during the controlled laboratory experiments to generate known values that are stored in the reference database 107 (FIG. 1) or 230 (FIG. 2). If the measured pressure is not the same as or within an acceptable deviation from the predetermined pressure, the pressure control unit 312 changes the pressure within the chamber 304 towards the predetermined pressure and then the sensor 310 again measures the pressure of the sample. However, in other examples, the size and/or volume of the chamber 304 may be associated with decreasing the pressure of the sample toward the predetermined pressure and, thus, the example apparatus 300 would not be provided with the pressure control unit 312.

Once the measured pressure is the same as or within an acceptable deviation from the predetermined pressure, the tunable light source 322 transmits light having one or more wavelength(s) through the gaseous portion of the sample within the chamber 304 and the fluid measurement unit 316 performs an optical measurement to measure characteristics or parameters of the gaseous portion of the sample. These measured characteristics and/or parameters are then compared to known characteristics and/or parameters stored in the reference database 107 (FIG. 1) or 230 (FIG. 2) to identify particular species and/or analyte(s) present in the fluid sample. In some examples, these characteristics and/or parameters may correspond to the presence and/or concentration of carbon dioxide, hydrogen sulfide, mercury, nickel, vanadium, sulfur, radon, polonium, barium, strontium, nitrogen, calcium, oxygen, helium, methane, ethane, tricarbon, diatomic carbon, or hydrocarbon within the fluid sample.

If a predetermined amount of time has expired or if a predetermined number of measurements have been obtained by the fluid measurement unit 316, the valve 308 may actuate to an open position and the pressure control unit 312 may increase the pressure within the chamber 304 to encourage the sample fluid to flow from the chamber 304 through the flowline section 307 and the opening 306 back into the flowline 302. Once the chamber 304 is emptied, the valve 308 may actuate to the closed position and the above described process may be repeated.

Figure 4:
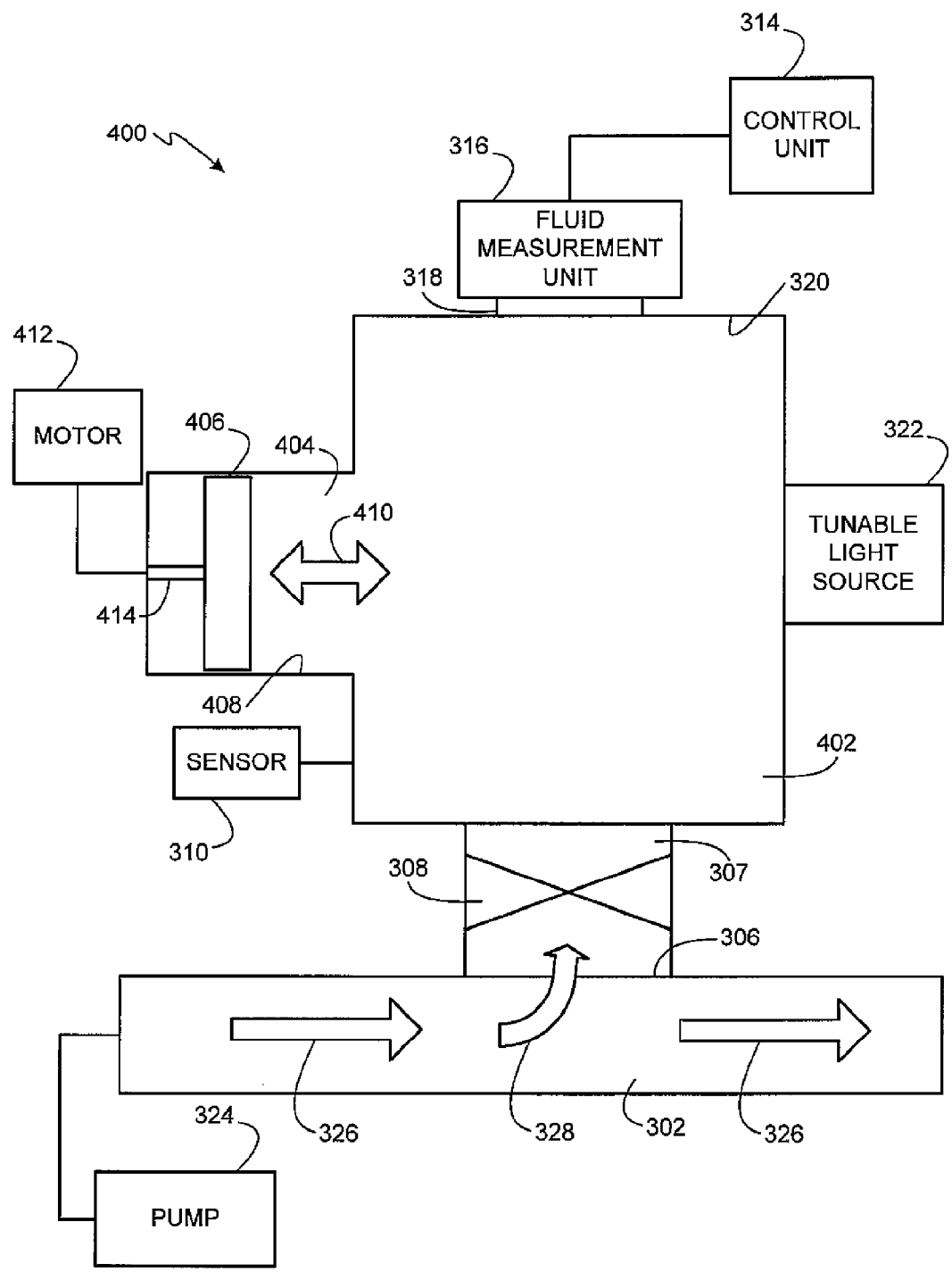
FIG. 4 is a schematic illustration of another example apparatus that may be used to implement or in conjunction with the fluid measurement unit of FIG. 2.

FIG. 4 illustrates an example apparatus 400 that depicts an example implementation of the pressure control unit 312 of FIG. 3 that may be used to implement the pressure control unit 212 of FIG. 2. The example apparatus 400 may include structure similar to the structure described above in the example apparatus 300 of FIG. 3. Reference numbers in FIG. 4 that are the same as those used in FIG. 3 correspond to structures that are similar or identical to those described in connection with FIG. 3. As such, the description corresponding to these reference numbers will not be repeated.

As described above, the example apparatus 400 includes the flowline 302 that is fluidly coupled to a chamber 402 at the opening 306 via the flowline section 307. The valve 308 is positioned adjacent the opening 306 within the flowline section 307 to control fluid flow between the flowline 302 and the chamber 402. The valve 308 may open to enable fluid to flow into or out of the chamber 402 or the valve 308 may close to retain at least a portion of the sample within the chamber 402.

To change a pressure of the sample within the chamber 402 toward a predetermined pressure, the chamber 402 defines a bore 404 in which a piston 406 is disposed. Specifically, the piston 406 is slidably and sealingly engaged to an inner diameter surface 408 of the bore 404 such that as the piston 406 extends and retracts within the bore 404 as indicated by arrow 410, the piston 406 changes the pressure within the chamber 402. The piston 406 is operatively coupled to a motor 412 via a rod 414.

In operation, once a sample is captured within the chamber 402, the sensor 310 measures the pressure of the sample. If there is an unacceptable deviation or difference between the measured pressure and the predetermined pressure, the motor 412 may extend or retract the piston 406 within the bore 404 to change the pressure within the chamber 402 toward the predetermined pressure. For example, if the pressure measured by the sensor 310 is 1.1 bar and the predetermined pressure is 1.5 bar, the motor 412 may extend the piston 406 within the bore 404 to increase the pressure within the chamber 402 toward the predetermined pressure. Alternatively, if the pressure measured by the sensor 310 is 1.9 bar and the predetermined pressure is 1.5 bar, the motor 412 may retract the piston 406 within the bore 404 to increase the volume of the chamber 402 and, thus, decrease the pressure within the chamber 402 toward the predetermined pressure.

As described above, once the measured pressure is the same as or within an acceptable deviation from the predetermined pressure, the tunable light source 322 transmits light having one or more wavelength(s) through the gaseous portion of the sample within the chamber 402, and the fluid measurement unit 316 performs an optical measurement to measure characteristics or parameters of the gaseous portion of the sample.

If a predetermined amount of time has expired or if a predetermined number of measurements have been obtained by the fluid measurement unit 316, the valve 308 may actuate to an open position and the motor 412 may fully extend the piston 406 within the bore 404 to increase the pressure within the chamber 304 to encourage the sample fluid to flow from the chamber 402 through the flowline section 307 and the opening 306 back into the flowline 302. Once the chamber 402 is emptied, the valve 308 may actuate to the closed position and the above-described process may be repeated.

Figure 5:
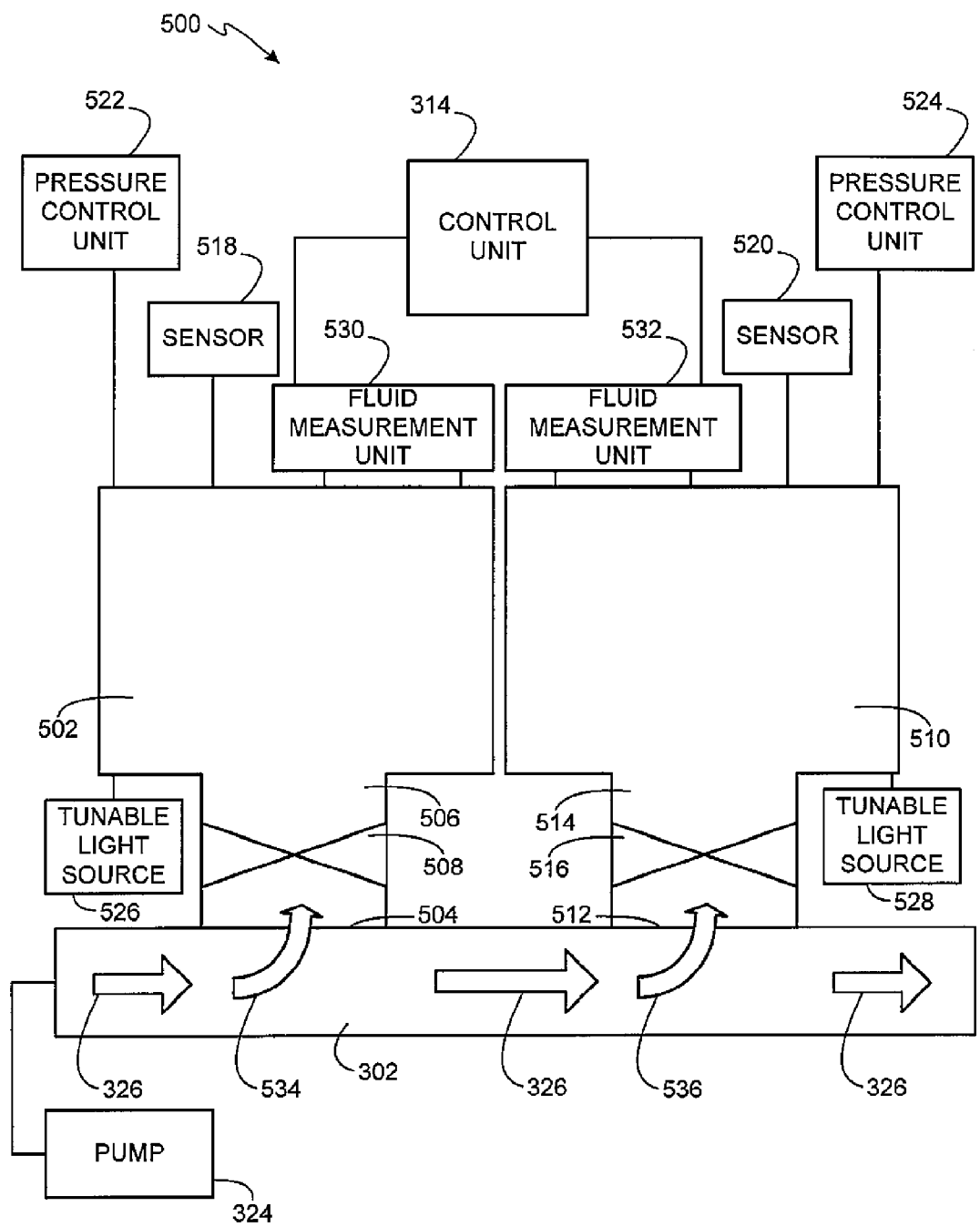
FIG. 5 is a schematic illustration of another example apparatus that may be used to implement the example apparatus of FIG. 3 in a series configuration.

FIG. 5 illustrates an example apparatus 500 that may be used to implement the example apparatus 300 (FIG. 3) in a series configuration. The example apparatus 500 may include structure similar to the structure described above in the example apparatus 300 of FIG. 3. Reference numbers in FIG. 5 that are the same as those used in FIG. 3 correspond to structures that are similar or identical to those described in connection with FIG. 3. As such, the description corresponding to these reference numbers will not be repeated.

The example apparatus 500 includes the flowline 302 that is fluidly coupled to a first chamber 502 at a first opening 504 via a first flowline section 506. A first valve 508 is positioned adjacent the first opening 504 within the first flowline section 506 to control fluid flow between the flowline 302 and the first chamber 502. Similarly, the flowline 302 is fluidly coupled to a second chamber 510 at a second opening 512 via a second flowline section 514. A second valve 516 is positioned adjacent the second opening 512 within the second flowline section 514 to control fluid flow between the flowline 302 and the second chamber 510. The first and second valves 508 and 516 may open to enable a fluid to flow into or out of the chambers 502 or 510 or the valves 508 and 516 may close to retain a portion of the sample within the respective chambers 502 and 510.

To measure the pressure of the sample within the first or second chambers 502 and 510, the example apparatus 500 is provided with a first sensor 518 and a second sensor 520. The first and second sensors 518 and 520 may be used to implement the sensor 310 of FIG. 3 or the sensors 216 of FIG. 2. Additionally, to change a pressure of the sample within the first or second chambers 502 and 510 toward a predetermined pressure, the example apparatus 500 is provided with a first pressure control unit 522 and a second pressure control unit 524. The first and second pressure control units 522 and 524 may be used to implement the pressure control units 212 (FIG. 2) or 312 (FIG. 3). However, as discussed above, the size and/or volume of the chambers 502 and 510 may be associated with decreasing the pressure of the sample toward the predetermined pressure and, thus, in this example implementation, the example apparatus 500 would not be provided with the pressure control units 522 and 524.

To transmit a light wavelength or a range of light wavelengths through a portion of the sample within the first chamber 502 or the second chamber 510, the example apparatus 500 is provided with a first tunable light source 526 and a second tunable light source 528 that may be implemented using a temperature controlled tunable diode laser, a temperature controlled broadband fiber light source, an amplified spontaneous emission source, a temperature controlled microelectromechanical system (MEMS) tunable filter or a temperature controlled tunable fiber laser. The first and second tunable light sources 526 and 528 may be used to implement the tunable light source 322 of FIG. 3. Additionally, as described above, to measure a characteristic of a portion of the sample once the measured pressure is the same as or within an acceptable deviation from the predetermined pressure, the example apparatus 500 is provided with a first fluid measurement unit 530 and a second fluid measurement unit 532. The first and second fluid measurement units 530 and 532 may be used to implement the fluid measurement unit 214 (FIG. 2) or 316 (FIG. 3). The first fluid measurement unit 530 may be similar or different from the second fluid measurement unit 532. If the fluid measurement units 530 and 532 are different from one another, each of the fluid measurement units 530 and 532 may be operable under different pressures and/or conditions. In some example implementations, the first fluid measurement unit 530 may be a wavelength modulation spectrometer and the second fluid measurement unit 532 may be a cavity ring-down spectrometer. Alternatively, in some example implementations, the first and second fluid measurement units 530 and 532 may both be infrared spectrometers.

In operation, the pump 324 pumps fluid (e.g., formation fluid) through the flowline 302 in a direction generally indicated by arrows 326. As the fluid moves through the flowline 302, the first valve 508 or the second valve 516 may actuate to an open position to enable a sample of the fluid to flow into the first chamber 502 and/or the second chamber 510 in a direction generally indicated by arrows 534 and 536. As the sample enters the first chamber 502 and/or the second chamber 510, the density and pressure of the sample reduces, which may induce a phase separation of a portion of the sample within the chamber 502 or 510. In some example implementations, the example apparatus 500 may actuate the first and second valves 508 and 516 substantially simultaneously to perform different measurements on substantially the same fluid sample. For example, the first fluid measurement unit 530 may be calibrated to measure light wavelengths in a first spectral range emitted by the first tunable light source 526 and the second fluid measurement unit 532 may be calibrated to measure light wavelengths in a second spectral range emitted by the second tunable light source 528. The first and second spectral ranges may be associated with different species and/or analyte(s) within the sample and, thus, a more thorough analysis of the species and/or analyte(s) present within the fluid sample may be conducted.

Alternatively, the example apparatus 500 may temporarily offset the actuation of the first valve 508 relative to the second valve 516 to ensure that measurements are performed continuously on a fluid in either the first chamber 502 or the second chamber 510. For example, the first valve 508 may actuate to an open position to enable a sample of the fluid to flow into the first chamber 502 while the second valve 516 is in a closed position and the second fluid measurement unit 532 is measuring characteristics and/or parameters of a portion of the sample within the second chamber 510.

If a predetermined amount of time has expired or if a predetermined number of measurements have been obtained by either the first fluid measurement unit 530 or the second fluid measurement unit 532, the first valve 508 and/or the second valve 516 may actuate to an open position and the respective pressure control unit 522 or 524 may increase the pressure within the chamber 502 or 510 to encourage the fluid to flow from the chamber 502 or 510 back into the flowline 302. Once the chamber 502 or 510 is emptied, the valve 508 or 516 may actuate to the closed position and the above described process may be repeated.

However, in some examples, the example apparatus 500 may not be provided with the pressure control units 522 and 524 because of the limited space available within the wireline tool 100 (FIG. 1) or the pressure control units 522 and 524 may not be able to sufficiently increase the pressure within the chamber 502 or 510 to encourage the fluid to flow out of the chambers 502 or 510. In this example, a first sample may be obtained for measurement by the first fluid measurement unit 530 at a first time and a second sample may be obtained for measurement by the second fluid measurement unit 532 at a second time, which may be different from the first time. In either case, after a predetermined number of measurements have been obtained by either the first fluid measurement unit 530 or the second fluid measurement unit 532, the sample remains in the respective chamber 502 or 510 until, for example, the wireline tool 100 (FIG. 1) is removed from the wellbore 102.

Figure 6:
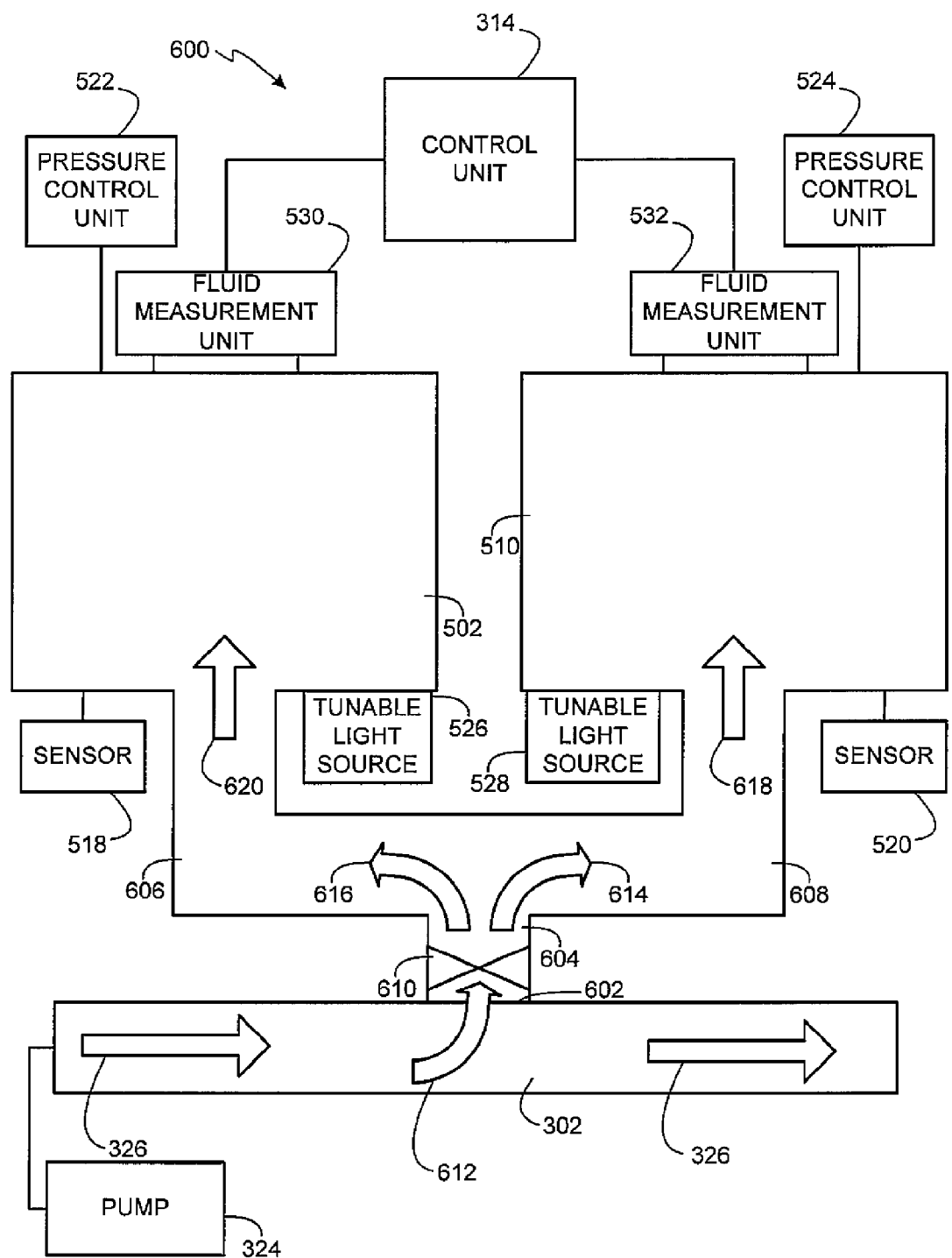
FIG. 6 is a schematic illustration of another example apparatus that may be used to implement the example apparatus of FIG. 3 in another configuration.

FIG. 6 illustrates an example apparatus 600 that may be used to implement the example apparatus 300 (FIG. 3) in an alternative configuration. The example apparatus 600 may include structure similar to the structure described above in the example apparatus 300 of FIG. 3 and the example apparatus 500 of FIG. 5. Reference numbers in FIG. 6 that are the same as those used in FIG. 3 or 5 correspond to structures that are similar or identical to those described in connection with FIGS. 3 and 5. As such, the description corresponding to these reference numbers will not be repeated.

In contrast to the example apparatus 500 of FIG. 5, the example apparatus 600 includes the flowline 302 that is fluidly coupled to the first chamber 502 and the second chamber 510 at an opening 602 via a flowline section 604. Specifically, the flowline section 604 has a first flowline section 606 that is fluidly coupled to the first chamber 502 and a second flowline section 608 that is fluidly coupled to the second chamber 510. A valve 610 is positioned adjacent the opening 602 within the flowline section 604 to control fluid flow between the flowline 302 and the first and second chambers 502 and 510.

In operation, the pump 324, pumps fluid (e.g., formation fluid) through the flowline 302 in a direction generally indicated by arrows 326. As the fluid moves through the flowline 302, the valve 610 may actuate to an open position to enable a sample of the fluid to flow into the first chamber 502 and the second chamber 510 in a direction generally indicated by arrows 612, 614, 616, 618 and 620. As the sample enters the first chamber 502 and the second chamber 510, the density and pressure of the sample is reduced which, in turn, may induce a phase separation of a portion of the sample within the chambers 502 and 510. The first fluid measurement unit 530 may be the same as or different from the second fluid measurement unit 532. In some example implementations, the first fluid measurement unit 530 may be calibrated to measure light wavelengths in a first spectral range emitted by the first tunable light source 526 and the second fluid measurement unit 532 may be calibrated to measure light wavelengths in a second spectral range emitted by the second tunable light source 528. The first and second spectral ranges may be associated with different species and/or analyte(s) within the sample and, thus, a more thorough analysis of the species and/or analyte(s) present within the fluid sample may be conducted.

If a predetermined amount of time has expired or if a predetermined number of measurements have been obtained by either the first fluid measurement unit 530 or the second fluid measurement unit 532, the valve 610 may actuate to an open position and the pressure control units 522 and/or 524 may increase the pressure within the chambers 502 or 510 to encourage the fluid to flow from the chambers 502 and 510 back into the flowline 302. Once the chambers 502 and 510 are emptied, the valve 610 may actuate to the closed position and the above described process may be repeated.

Figure 7:
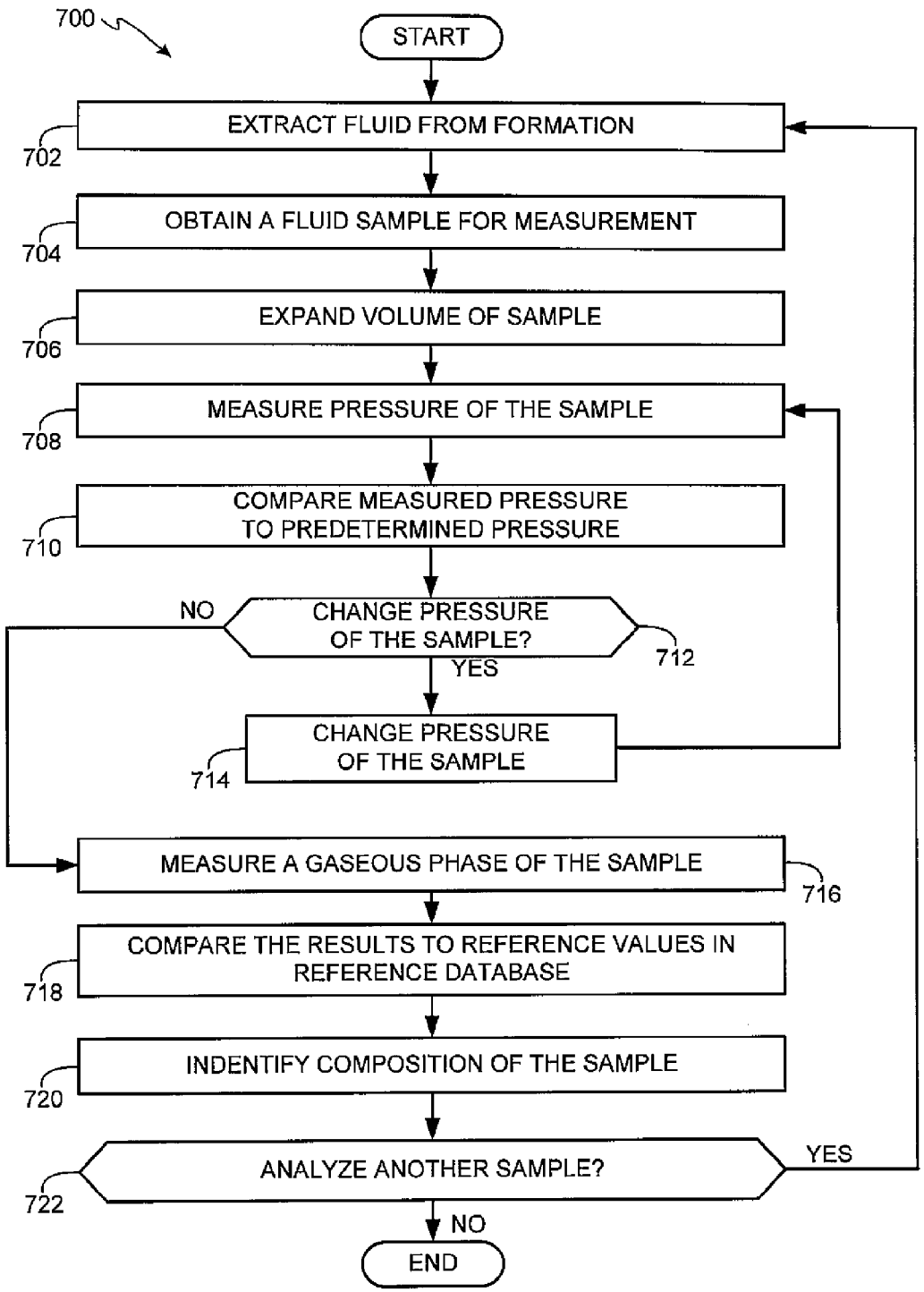
FIG. 7 is a flow diagram of an example method that may be used in conjunction with the example apparatus described herein to identify fluid components in formation fluid samples.

FIG. 7 is a flowchart of an example method 700 that can be used in conjunction with the example apparatus described herein to draw and analyze formation fluid samples from a subterranean formation (e.g., the formation F of FIG. 1). The example method of FIG. 7 may be used to implement the example formation tester 114 of FIG. 1, the formation sampling tool 200 of FIG. 2, and the example apparatus 300, 400, 500 and 600 of FIGS. 3, 4, 5 and/or 6. The example method of FIG. 7 may be implemented using software and/or hardware. In some example implementations, the flowchart can be representative of example machine readable instructions, and the example method of the flowchart may be implemented entirely or in part by executing the machine readable instructions. Such machine readable instructions may be executed by one or both of the electronics and processing system 106 (FIG. 1) and/or the control unit 228 (FIG. 2). In particular, a processor or any other suitable device to execute machine readable instructions may retrieve such instructions from a memory device (e.g., a random access memory (RAM), a read only memory (ROM), etc.) and execute those instructions. In some example implementations, one or more of the operations depicted in the flowchart of FIG. 7 may be implemented manually. Although the example method is described with reference to the flowchart of FIG. 7, persons of ordinary skill in the art will readily appreciate that other methods to implement the example formation tester 114 of FIG. 1, the formation sampling tool 200 of FIG. 2, and the example apparatus 300, 400, 500 and 600 of FIGS. 3, 4, 5 and/or 6 to analyze formation fluid samples may additionally or alternatively be used. For example, the order of execution of the blocks depicted in the flowchart of FIG. 7 may be changed and/or some of the blocks described may be rearranged, eliminated, or combined.

The example method 700 may be used to draw and analyze formation fluids using, for example, the formation sampling tool 200 of FIG. 2. Initially, the probe assembly 202 (FIG. 2) extracts (e.g., admits, draws, etc.) fluid from the formation F (block 702) and the valve 232 (FIG. 2) actuates to an open position enabling a sample of the fluid to flow into the chamber 210 (FIG. 2) from the flowline 224 (FIG. 2) (block 704). As the sample enters the chamber 210 (FIG. 2), the volume of the sample increases and/or expands (block 706), which decreases the density and the pressure of the sample. Once a predetermined amount of time has expired or a predetermined amount of the fluid has entered the chamber 210 (FIG. 2), the valve 232 (FIG. 2) is actuated to the closed position and the sensor 216 (FIG. 2) measures the pressure of the sample (block 708). The control unit 228 (FIG. 2) then compares the measured pressure to a predetermined pressure (block 710) and determines whether or not to change the pressure of the sample within the chamber 210 (FIG. 2) (block 712). If the measured pressure is not the same as or within an acceptable deviation from the predetermined pressure, the pressure control unit 212 (FIG. 2) changes the pressure within the chamber 210 (FIG. 2) toward the predetermined pressure (block 714) and the pressure of the sample is again measured as described in connection with block 708. However, as discussed above, the size and/or volume of the chamber 210 (FIG. 2) may be associated with decreasing the pressure of the sample toward the predetermined pressure. In such an example implementation, the formation sampling tool 200 (FIG. 2) would not be provided with the pressure control unit 212 (FIG. 2) and, thus, blocks 712 and 714 would not be applicable.

If the measured pressure is the same as or within an acceptable deviation from the predetermined pressure, the fluid measurement unit 214 (FIG. 2) measures a characteristic or a parameter of a gaseous phase of the sample within the chamber 210 (FIG. 2) (block 716). The measured characteristics and/or parameters (e.g., the results) are then compared to known characteristics and/or parameters stored in the reference database 107 (FIG. 1) or 230 (FIG. 2) (block 718). The composition (e.g., the species and/or analyte(s)) of at least a portion of the sample may be determined and/or identified (block 720) by matching the characteristics and/or parameters measured from the sample within the chamber 210 (FIG. 2) with the parameters and/or characteristics stored within the reference database 107 (FIG. 1) or 230 (FIG. 2) that are associated with known samples having known compositions.

The control unit 228 (FIG. 2) then determines whether it should analyze another formation fluid sample (block 722). For example, if the formation sampling tool 200 (FIG. 2) has drawn another formation fluid sample and the control unit 228 (FIG. 2) has not received an instruction or command to stop analyzing fluid, the control unit 228 (FIG. 2) may determine that it should analyze another fluid sample (block 722). Otherwise, the example process of FIG. 7 is ended.

FIG. 8 is a schematic diagram of an example processor platform P100 that may be used and/or programmed to implement the electronics and processing system 106, the control unit 228, the fluid measurement units 214, 316, 530 and 532, and/or the pressure control units 212, 312, 522, and 524. For example, the processor platform P100 can be implemented by one or more general purpose processors, processor cores, microcontrollers, etc.

The processor platform P100 of the example of FIG. 8 includes at least one general purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example methods and apparatus described herein.

The processor P105 is in communication with the main memory (including a ROM P120 and/or the RAM P115) via a bus P125. The RAM P115 may be implemented by dynamic random-access memory (DRAM), synchronous dynamic random-access memory (SDRAM), and/or any other type of RAM device, and ROM may be implemented by flash memory and/or any other desired type of memory device. Access to the memory P115 and the memory P120 may be controlled by a memory controller (not shown).

The processor platform P100 also includes an interface circuit P130. The interface circuit P130 may be implemented by any type of interface standard, such as an external memory interface, serial port, general purpose input/output, etc. One or more input devices P135 and one or more output devices P140 are connected to the interface circuit P130.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. An apparatus to analyze a downhole fluid, comprising:
a chamber to decrease a density of at least a portion of a sample of a downhole fluid;
a sensor to measure a pressure of at least the portion of the sample in the chamber;
a fluid measurement unit to measure a characteristic of at least the portion of the sample based on a relationship between the pressure of at least the portion of the sample in the chamber and a predetermined pressure; and
a control unit to determine a parameter of the downhole fluid based on the characteristic.

2. The apparatus as defined in claim 1, wherein the portion of the sample is a fluid in a gaseous phase.

3. The apparatus as defined in claim 1, wherein the fluid measurement unit comprises at least one of a metal corrosion measurement unit, an optical reflection measurement unit, or a solid state gas sensor.

4. The apparatus as defined in claim 1, wherein the control unit is to compare the parameter to a known parameter to determine a composition of at least the portion of the sample.

5. The apparatus as defined in claim 1, wherein the chamber decreases the pressure of at least the portion of the sample below a bubble point pressure.

6. The apparatus as defined in claim 1, wherein the downhole fluid is at least one of a wellbore fluid or a fluid extracted from a subsurface formation.

7. The apparatus as defined in claim 1, wherein the downhole fluid is at least one of a heavy oil, a bitumen, a gas condensate, or a drilling fluid.

8. The apparatus as defined in claim 1, wherein the parameter of the downhole fluid is associated with the composition of the downhole fluid.

9. The apparatus as defined in claim 1, wherein the parameter of the downhole fluid is associated with at least one of carbon dioxide, hydrogen sulfide, mercury, nickel, vanadium, sulfur, radon, polonium, barium, strontium, nitrogen, calcium, oxygen, helium, methane, ethane, tricarbon, diatomic carbon, or hydrocarbon.

10. The apparatus as defined in claim 1, further comprising a fluid control device to enable the sample to flow into the chamber.

11. The apparatus as defined in claim 10, wherein the fluid control device is an injection valve.

12. The apparatus as defined in claim 1, wherein the chamber decreases the pressure of the portion of the sample to increase a number of absorption peaks associated with the portion of the sample.

13. The apparatus as defined in claim 12, wherein the absorption peaks are associated with one or more measurable characteristics of the downhole fluid.

14. The apparatus as defined in claim 1, further comprising a pressure control unit to change the pressure of at least the portion of the sample in the chamber based on the predetermined pressure.

15. The apparatus as defined in claim 14, wherein the pressure control unit comprises a piston assembly to slidably and sealingly engage a bore defined by the chamber, and wherein the piston assembly is to move relative to the bore in response to a difference between the pressure and the predetermined pressure.

16. The apparatus as defined in claim 1, wherein the fluid measurement unit comprises a spectrometer.

17. The apparatus as defined in claim 16, wherein the spectrometer is at least one of an infrared spectrometer, a tunable laser spectrometer, an acusto-optical tunable filter spectrometer, an optical absorption spectrometer, an LED spectrometer, a LED array spectrometer, a wavelength modulation spectrometer, a cavity ring-down spectrometer, an ultraviolet spectrometer, an ultraviolet-visible spectrometer, a near infrared spectrometer, a mid-infrared spectrometer, a UV/VIS/NIR spectrometer, or a plasma spectrometer.

18. A method of analyzing a downhole fluid, the method comprising:
    obtaining a sample of a downhole fluid;
    expanding the volume of the sample to decrease a density of at least a portion of the sample;
    measuring a pressure of at least the portion of the sample; and
    analyzing at least the portion of the sample to determine a parameter of the downhole fluid in response to a relationship between the pressure of at least the portion of the sample and a predetermined pressure.

19. The method as defined in claim 18, further comprising changing the pressure of at least the portion of the sample toward the predetermined pressure.

20. The method as defined in claim 18, wherein expanding the volume of the sample comprises vaporizing at least the portion of the sample.

21. The method as defined in claim 18, wherein expanding the volume of the sample comprises actuating a valve to enable the sample to flow into a chamber.

22. The method as defined in claim 18, wherein analyzing the portion of the sample comprises performing an optical measurement on the portion of the sample.

23. The method as defined in claim 18, wherein the portion of the sample is a fluid in a gaseous phase.

24. An apparatus for analyzing a downhole fluid, comprising:
    means for expanding a volume of a sample of a downhole fluid to decrease a density of at least a portion of the sample;
    means for measuring a pressure of at least the portion of the sample; and
    means for analyzing at least the portion of the sample to determine a parameter of the downhole fluid in response to a relationship between the pressure and a predetermined pressure.

25. The apparatus as defined in claim 24, wherein the means for expanding the volume of the sample comprises means for enabling the sample to flow into a chamber.

26. The apparatus as defined in claim 24, further comprising means for changing the pressure toward the predetermined pressure.

27. The apparatus as defined in claim 26, wherein the means for changing the pressure toward the predetermined pressure comprises a piston assembly to slidably and sealingly engage a bore defined by a chamber, wherein the piston assembly moves relative to the bore in response to a difference between the pressure and the predetermined pressure.

* * * * *